United States Patent [19]

Gardos

[11] Patent Number: 4,535,585
[45] Date of Patent: Aug. 20, 1985

[54] CAP REMOVAL DEVICE FOR A CELLULAR SAMPLE TREATMENT APPARATUS

[75] Inventor: Ivan Gardos, Montreal, Canada

[73] Assignee: Biomatics Inc., Montreal, Quebec, Canada

[21] Appl. No.: 587,660

[22] Filed: Mar. 8, 1984

[51] Int. Cl.³ .............................................. B65B 1/04
[52] U.S. Cl. ...................................... 53/247; 53/308;
53/381 A; 81/3.2
[58] Field of Search .................... 81/3.2, 3.1 R, 3.1 B,
81/3.1 C, 3.1 D; 53/308, 381 A, 247, 249

[56] References Cited

U.S. PATENT DOCUMENTS

| 774,378 | 11/1904 | Carter | 53/381 A |
|---|---|---|---|
| 2,837,055 | 6/1958 | Whitehead | 118/500 |
| 2,990,073 | 6/1961 | Textor | 53/381 A |
| 3,302,607 | 2/1967 | Kobernick | 118/11 |
| 3,356,096 | 12/1967 | Davis et al. | 134/58 |
| 3,479,196 | 11/1969 | Heimann | 117/3 |
| 3,545,174 | 12/1970 | Randrup | 81/3.2 |
| 3,809,008 | 5/1974 | Takahaski | 118/6 |
| 3,880,014 | 6/1975 | Kinney et al. | 427/4 |
| 4,103,722 | 8/1978 | Zollinger | 141/70 |

FOREIGN PATENT DOCUMENTS 764897 8/1967 Canada .
847306 7/1970 Canada .

Primary Examiner—James L. Jones, Jr.
Attorney, Agent, or Firm—Larson and Taylor

[57] ABSTRACT

A cap removal device is provided for a cellular sample treatment apparatus. The device avoids the necessity to manually remove a cap and allows an automated sequence of steps to be carried out. The device is utilized in an apparatus for treating samples of cellular materials wherein the samples are contained in a stack of sample holders and fit in a stack holding tube, open at the top with a removable cap. A transfer tube having a bottom opening to fit on the top of the stack holding tube is provided and has a drive system to move the stack from the stack holding tube to the transfer tube. The improvement includes a fork attached to the drive system for the stack removal, and a button or grooved member on the cap for engagement by the fork so that when the drive system moves upwards it lifts the cap with it.

3 Claims, 8 Drawing Figures

CAP REMOVAL DEVICE FOR A CELLULAR SAMPLE TREATMENT APPARATUS

The present invention relates to an apparatus for treating animal and vegetable tissue samples for inspection under an electron microscope. More specifically, the present invention relates to a novel cap removal device to remove a cap from a stack holding tube containing a stack of tissue sample holders.

In the preparation of animal and vegetable tissue samples for examination under an electron microscope, it is necessary to treat the tissue sample and this is done by removing the water in a series of chemical dehydration steps and then replacing the water removed from the tissue sample with an epoxy resin. The addition of an epoxy resin hardens the sample so that it can then be sliced into thin sections suitable for examination under the microscope.

The process of replacing water in a tissue sample with epoxy is a complex process which includes placing the samples into corrosive chemicals and/or buffering solutions. The tissue sample is placed in a number of different solutions, in a series of steps involving heating and cooling which can take from three to four hours. If this process is done manually then it requires almost constant attention which consumes considerable operator time. It is most important that these steps be followed in the correct sequence to ensure that the tissue is not damaged by removal of the water and replacement with epoxy.

Automated processes and devices have been made to treat animal and vegetable tissue samples. In some known devices corrosive liquids are pumped into tubes containing tissue samples. It has been found that the pumping of these corrosive liquids is not only dangerous, but also wasteful. because after the pumping step the fluids have to be discharged. Furthermore, the tubes and pumps through which the liquid passes tend to corrode and, therefore, must be replaced frequently.

It is an object of the present invention to provide an apparatus for preparing animal and vegetable tissue samples for inspection under an electron microscope which is completely automated and can be preset to start while unattended. In this way, tissue samples which are needed in the morning can be left in the device which is programmed to start treatment four or five hours before the operator comes into the laboratory, so that the samples are ready for being sliced into suitable specimens for inspection. Furthermore, it is another object of the invention to provide an apparatus which does not have a series of tubes and pumps to move the chemicals to the sample, but rather which is arranged to move the tissue samples from one disposable container to another containing the necessary chemicals. The apparatus moves the tissue samples to the chemicals rather than the chemicals to the samples.

The present invention provides in an apparatus for treating samples of cellular materials wherein the samples are contained in a plurality of sample holders joined together to form a stack, the apparatus including at least one stack holding tube, open at the top, having a removable cap, positioning means to move the stack holding tube between a treatment position and a cap removal position, a transfer tube having a bottom opening positioned in the treatment position above the stack holding tube, and means to move the stack from the stack holding tube to the transfer tube the improvement of a cap removable device comprising, a fork means attached to the means to move the stack from the stack holding tube to the transfer tube fork mating means on the removable cap, the fork means engaging with the fork mating means when the means to move the stack is at a predetermined position, and the stack holding tube is moved to the cap removal position, the cap is lifted when the means to move the stack is raised.

In a preferred embodiment a plurality of stack holding tubes are positioned in a circle about a vertical axis of a rotatable carousel, and including drive means for rotating the carousel, lateral movement means for moving the carousel into at least three positions representing rotating position, the cap removal position and the treatment position, and wherein the fork means engages with the cap when the stack holding tube on the carousel is moved from the rotating position to the cap removal position. In another embodiment the means to move the stack from the stack holding tube to the transfer tube comprises a movable magnetic coil about the transfer tube which magnetizes a magnetizable member at the top of the stack, and the fork means for lifting the cap is connected to the movable magnetic coil.

In drawings which illustrate embodiments of the invention:

FIG. 4A is a detailed sectional view taken at line 4A—4A of FIG. 4 showing the fork member for engaging a cap.

Figure 1:
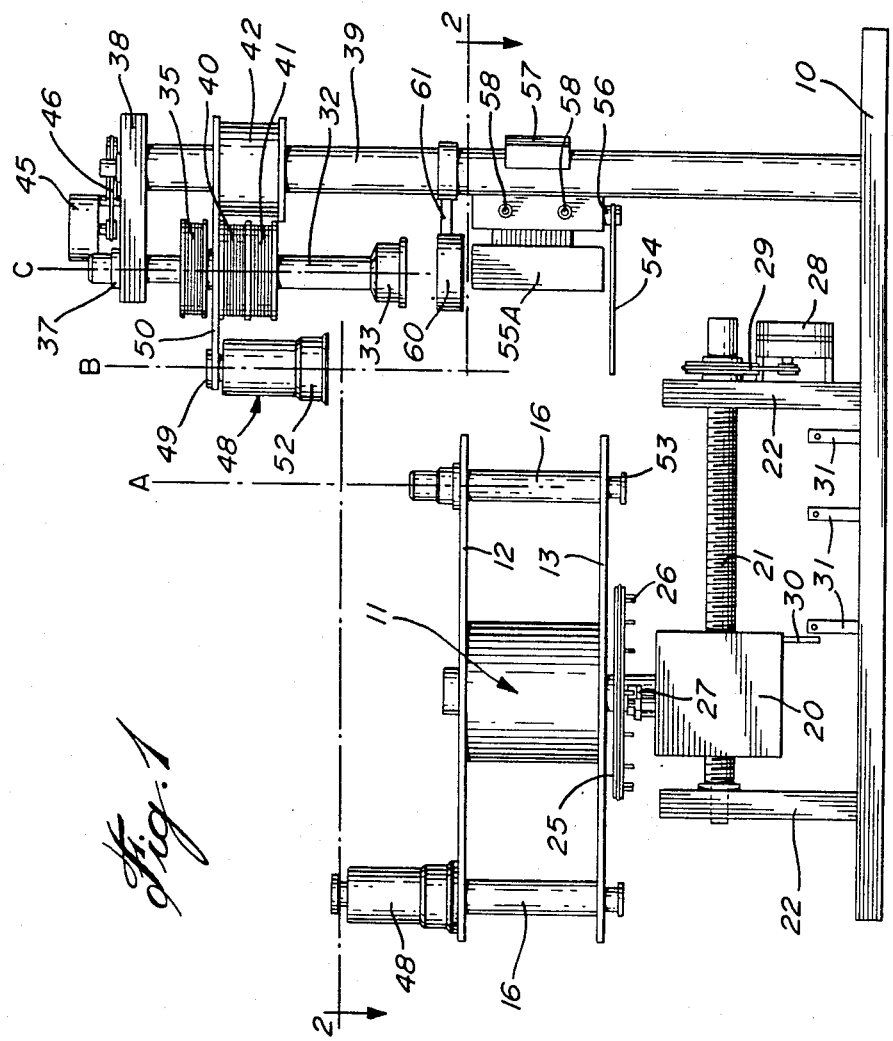
FIG. 1 is a side elevational view of one embodiment of an apparatus for treating samples of cellular materials.
Figure 2:
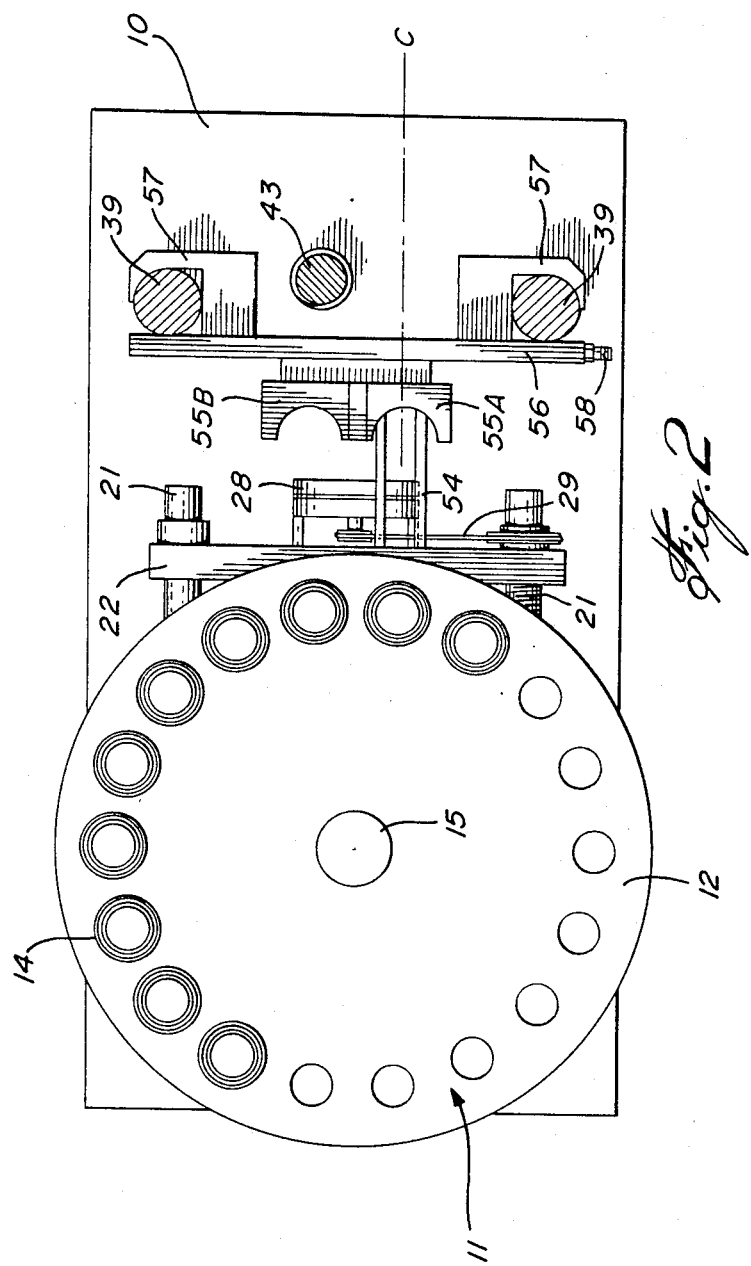
FIG. 2 is a top sectional view taken at line 2—2 of FIG. 1.
Figure 3:
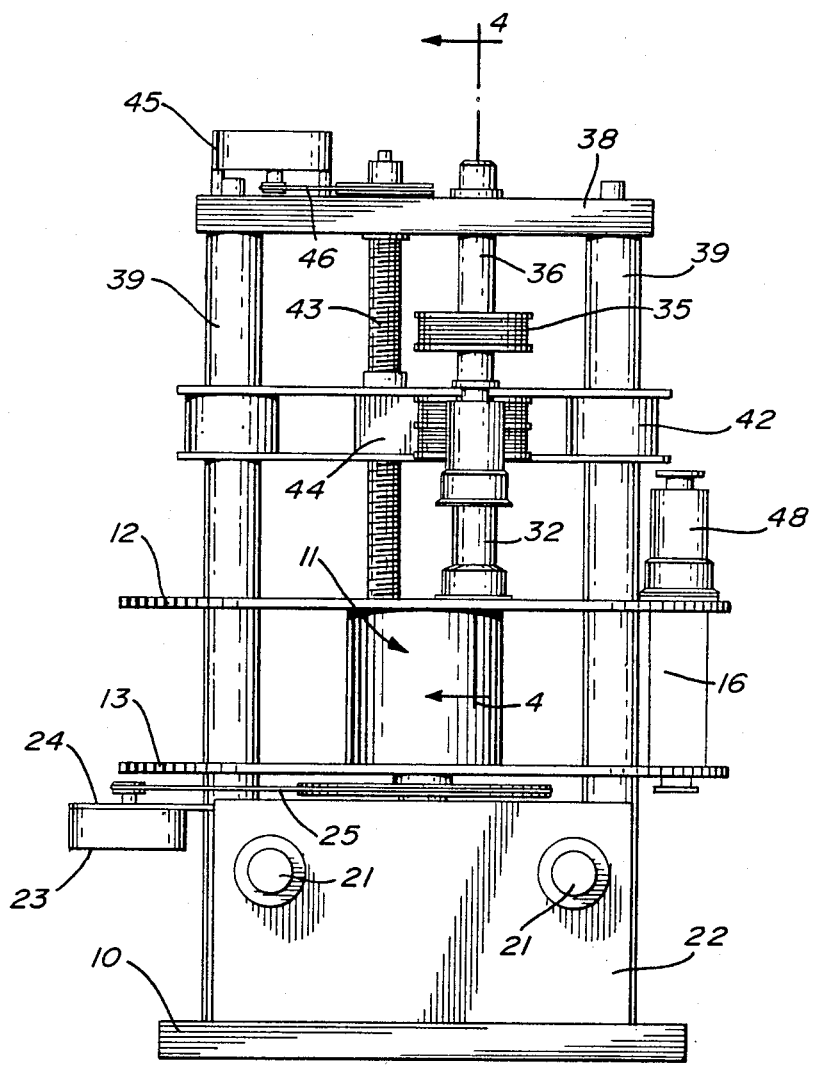
FIG. 3 is a front end view of the apparatus shown in FIG. 1.

Referring now to the drawings, an apparatus for treating samples of cellular material is shown in FIGS. 1, 2 and 3 having a base plate 10 on which is mounted a carousel 11 with mechanisms to rotate the carousel, and move the carousel in a linear direction. The carousel has a top plate 12 and a bottom plate 13 and a plurality of holes 14 in both plates 12, 13 located in a circle about a rotating axis 15. The holes 14 hold disposable plastic stack holding tubes 16 for a stack of sample holders. In one particular embodiment there are twenty two holes 14 to hold plastic stack holding tubes. The stack holding tubes 16 contain the different chemicals for the treatment process.

The carousel 11 is supported from a carriage block 20 which moves linearly backwards and forwards on two shafts 21, one a screw shaft and the other a hardened smooth shaft. The shafts are supported by side support plates 22, mounted on the base plate 10. The carousel 11 has a rotate motor 23 mounted by means of a bracket 24 on the carriage block 20. The rotate motor 23 is a stepping motor and has a belt drive driving a pulley wheel 25 attached to the underside of the carousel 11 to rotate the carousel 11. Index pins 26 extend down from the pulley wheel 25 and are arranged to interrupt an integral light emitter sensor 27 positioned on the carriage block 20 to index the carousel 11 from one hole 14 to the next.

The linear movement of the carousel is provided by a linear motor 28 which through a pulley drive 29 rotates the screw shaft 21 moving the carriage block 20 backwards and forwards. As illustrated in FIG. 1, the carriage block 20 may be positioned so that a stack holding tube 16 is in one of three positions, position A being the carousel rotation position, position B being the cap removal position and position C being the treatment position. The linear motor 28 is a stepping motor and a positioning pin 30 extending from the carriage block 20 is arranged to interrupt three integral light emitter sensors 31 positioned on the base plate 10 representing positions A, B and C. A top transfer tube 32 having a lower flange 33 to engage and snap onto a stack holding tube 16 in the treatment position C on the carousel 11 is positioned above the carousel 11. As seen in more detail in FIG. 4, the top transfer tube 32 which is preferably made of polyethylene or other suitable material, is connected at its top by means of a screw thread 34 to the core of a top hold magnetic coil 35 and has a shaft 36 extending from the top coil 35 passing through a bushing 37 in a top support plate 38. The top support plate 38 is held upright by two posts 39 which are attached to the base plate 10. Two magnetic transfer coils 40, 41 surround the top transfer tube 32 and are connected to a traveller member 42 which fits over the two posts 39 and is arranged to slide up and down on these posts 39. A drive shaft 43 having a screw thread thereon parallel to the posts 39 has an internally threaded block 44 in the traveller member 42, thus rotation of the shaft 43 moves the traveller member 42 up and down so that the magnetic transfer coils 40 and 41 move up and down the top transfer tube 32. The threaded shaft 43 is rotated by an up and down motor 45 mounted on the top support plate 38 and driven through a pulley drive 46 to position the traveller member 42 and thus the magnetic coils 40, 41 about the top transfer tube 32.

Figure 4:
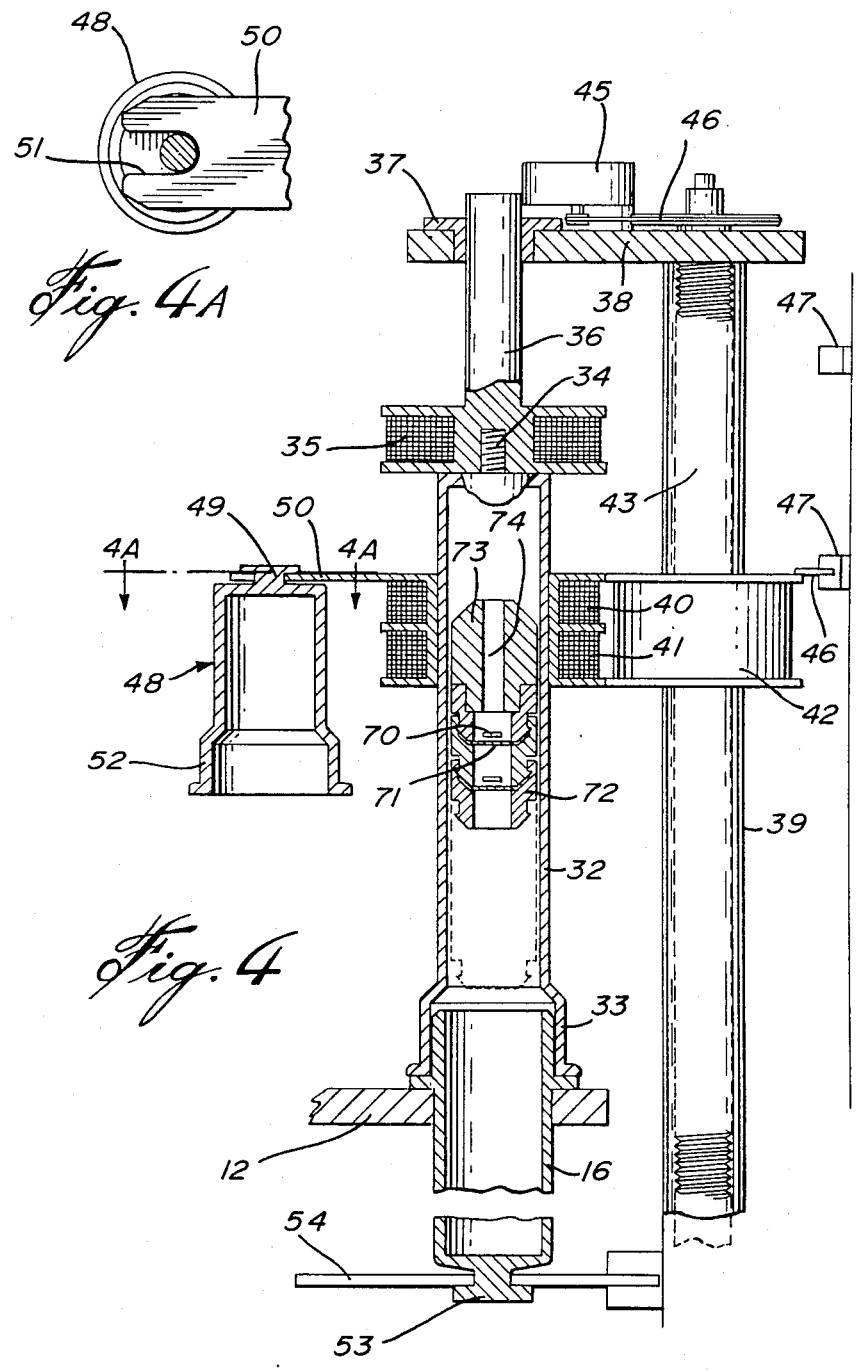
FIG. 4 is a sectional view taken at line 4—4 of FIG. 3 showing a stack holding tube in the treatment position.

The up and down motor 45 is a stepping motor, and as shown in FIG. 4, a positioning pin 46 on the traveller member 42 interrupts two integral light emitter sensors 47 controlling the top and bottom positions of the travelling member 42.

When the magnetic coils 40, 41 reach the top of the top transfer tube 32, the top magnetic coil 35 and the shaft 36 is pushed upwards so that the shaft 36 slides in bushing 37 and the top tube 32 is raised above the stack holding tube 16 in the carousel 11.

The stack holding tube 16 generally has a cap 48 over the top of the stack holding tube 16 to seal it when not in the treatment position. The cap 48 has a top button 49 which may be engaged by a fork member 50 attached to the travelling member 42 at the top of the magnetic transfer coils 40, 41. The fork member 50 as shown in FIG. 4A has a slot 51 to engage with the top button 49 on the cap 48. The cap 48 has a flange 52 similar to the flange 33 on the bottom of the top transfer tube 32 which engages and snaps onto the top of the stack holding tube 16.

At the bottom of each stack holding tube 16 is a lower button 53 which engages with a hold down fork 54 fixed to the frame of the device. The hold down fork 54 holds the stack holding tube 16 when in position B and C so the tube 16 is held down when the cap 48 is removed and when the top transfer tube 32 is removed.

In the treatment position C below the top tube 30 is a heating and cooling jacket 55A having a contoured groove to support a stack holding tube 16.

A second heating and cooling jacket 55B, also having a contoured groove is located adjacent the first jacket 55A so that a stack holding tube in a preprocess position can be heated or cooled as required. The temperatures of the two jackets, 55A and 55B are controlled independently by closed loop systems monitoring temperature sensors (not shown) in the two jackets 55A and 55B.

Cooling coils are included in the support members 56 which are attached by clamps 57 to the posts 39. Connections 58 are provided for cooling water to the cooling coils.

Thus a stack holding tube 16 can be preheated or precooled in the preprocess position before being moved to the treatment position C. A drip tray 60 is provided to rest underneath the top tube 30 when the carousel 11 is not moved so that there is a stack holding tube 16 in the treatment position C. The drip tray 60 has a spring loaded arm 61 and when the carousel 11 is moved so that there is a stack holding tube 16 in the treatment position C, the drip tray 60 is pushed to one side.

Tissue samples 70 to be treated are shown in FIG. 4, each sitting on a stainless steel screen 71 of an individual sample holder 72, made of plastic material and arranged to snap together into a stack of sample holders 72. At the top of the stack is a magnetizable member 73 made of magnetic stainless steel with a hole 74 in the centre thereof for venting purposes. In one embodiment, up to thirteen individual sample holders 72 may be snapped together to form a stack and joined to the top magnetizable member 73. Each holder 72 can contain at least one tissue sample 70 to be treated.

In operation, the sample holders 72 are assembled one by one with the tissue samples 70 therein resting on the stainless steel screens 71 between the holders 72. As the holders are assembled, they are filled with liquid solution to remove air from within the stack of specimen holders 72. It is important that the tissue samples are not allowed to dry out, as a dried out sample is not suitable for electron microscope examination. The stack of holders 72 with the top magnetizable member 73 joined together is then moved into a first stack holding tube 16, a cap 48 positioned on the tube 16 which is then placed in the carousel 11. Other stack holding tubes 16 also on the carousel are filled with the necessary liquids for removing water and treating the specimens 70. The carousel 11 is rotated until the tube 16 holding the stack of specimen holders 72 is lined up in position A. The travel member 42 is brought down to a cap engaging height by the up and down motor 45, so that the fork member 50 is positioned for the slot 51 to engage with the button 49 on the cap 48. The carousel 11 is then moved linearly by the linear motor 28 so the tube 16 is moved to position B when the slot 51 of the fork member 50 engages with the cap 48. The up and down motor 45 for travelling member 42 then raises the cap 48 off the stack holding tube 16 in the carousel 11, the tube hold down fork 54 anchoring the stack holding tube 16 in the carousel. The carousel 11 is then moved linearly by the linear motor 28 so the tube 16 is moved to position C pressing the tube 16 into the heating and cooling jacket 55A, and the up and down motor 45 for the travel member 42 lowers the top transfer tube 32 onto the top of the stack holding tube 16 and snaps the two tubes together. The two magnet transfer coils 40, 41 are then activated. One coil 40 is on all the time, the second coil 41 pulses which produces a vibratory effect on the magnetizable member 73 and consequently on the stack of holders 72 with the tissue samples 70 therein. The intensity of vibration can be varied as desired for different liquids. The travel member 42 is slowly raised by the up and down motor 45 and the magnetic coils 40, 41 produce a magnetic field to hold the magnetizable member 73 so that it moves upwards and brings the stack of holders 72 with it. The vibratory effect breaks up the surface tension of liquid within the stack so the liquid remains in the stack holding tube 16. When the coils 40, 41 reach the top of the top transfer tube 32, the travelling member 42 continues upwards raising the top transfer tube 32 so it disengages from the stack holding tube 16 in the carousel 11. The top holding coil 35 is then turned on and the two moving coils 40, 41 are turned off so that the magnetizable member 73 is held in the magnetic field of the top holding coil 35 and the stack of holders 72 remains at the top of the top transfer tube 32. The linear motor 28 then moves the carousel 11 back to position B. The travel member 42 is then lowered by the up and down motor 45 so that the cap 48 is replaced on the stack holding tube 16. The linear motor 28 then moves the carousel 11 back to position A and the rotate motor 23 rotates the carousel 11 by one step. A further sequence occurs and another tube is moved forward. The cap 48 may be removed in the same manner and the tube is then placed in the treatment position C. The stack of holders 72 is dropped into the new tube 16 by turning off the top holding coil. The agitation of the stack of holders 72 in the new tube is achieved by pulsing the magnetic transfer coils 40, 41 according to a predetermined rate and intensity. The heating and cooling jackets 55A and 55B may be utilized for predetermined time periods in the treatment position and in the pretreatment position according to a particular program.

When the linear motor 28 moves the carousel 11 away from the treatment position, a drip tray 60 swings into place on a spring loaded arm 61 to catch any drips of liquid which may drop from the stack of holders 72 in the top transfer tube 32. When the treatment sequence is finished, and after the stack of holders 72 has been returned to the original stack holding tube 16, the linear motor 28 moves the carousel 11 to position A and the stack of holders 72 may be removed from the stack holding tube 16, dismantled, and the specimens 70 taken for further processing.

All the movements of the three motors rotating the carousel, linearly moving the carousel and raising and lowering the transfer tube 32 are limited by optical sensors, in the embodiment shown wherein a pin interrupts a beam of light. It will be apparent to those skilled in the art that other types of limit switches can control the indexing and length of movements.

An exhaust fan may be included with the apparatus with the modular unit having an enclosure surrounding it, the exhaust fan removing any toxic or obnoxious fumes.

All the stack holding tubes used to hold the stack of holders 72 and the different chemicals may be thrown out after each preparation run. Furthermore, the top transfer tube 32 is also thrown out after each run, so there is no need to clean tubes or containers, all items touched by the chemicals are disposable. The mechanical function of the apparatus is controlled by a separate controller contained in a separate container.

One controller may control up to eight different mechanical modules, all programmed to perform different or similar steps at the same time or at different times. Thus the system is a modular system allowing up to eight separate modules.

Figure 5:
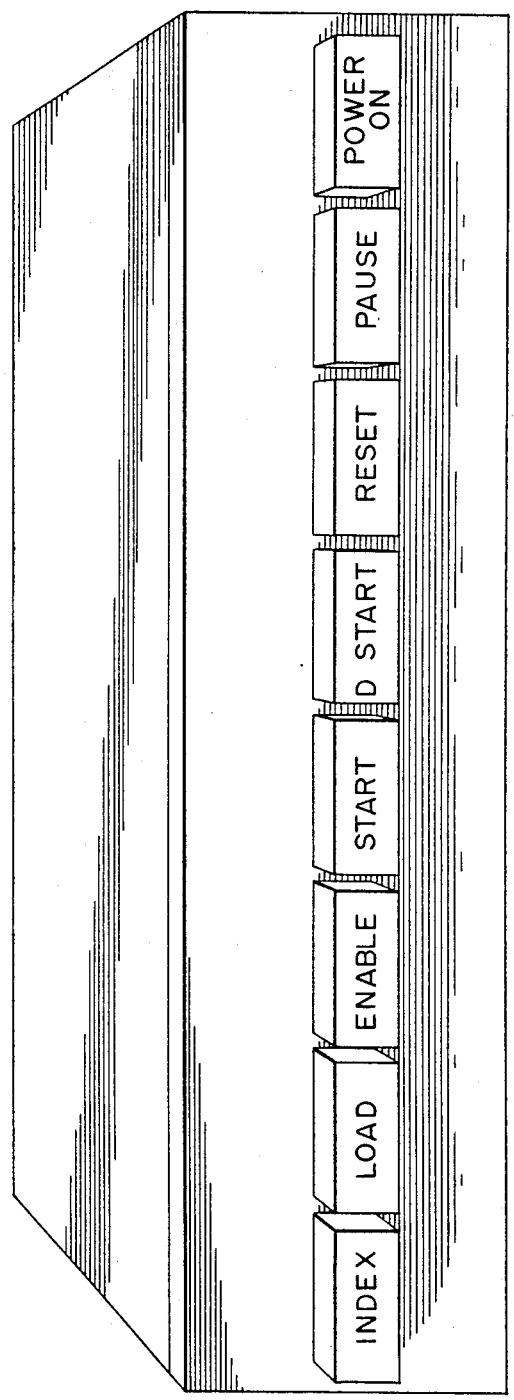
FIG. 5 is an isometric view of a control panel for operating the apparatus of the present invention.

The push button controls for a mechanical module are indicated in FIG. 5, where the first push button, labelled "index" indexes the carousel to rotate one tube position for each depression. The "load" button returns the carousel so a first tube hole is always at the same position opposite the start switch. The "enable" button is a prerequisite before pressing the "start" button, and when the "start" button is depressed, the first tube hole is rotated in the carousel, a tube uncapped and then pressed into the temperature jacket awaiting a program to be executed from the controller, referred to as the central processing unit (CPU). The "D-start" button is the same function as the "start" button but includes a programmed time delay. The "reset" button stops whatever step is in process and return the first tube hole to the start position. The "pause" button suspends the times sequence occuring and the "power on" is an indicator light.

Figure 6:
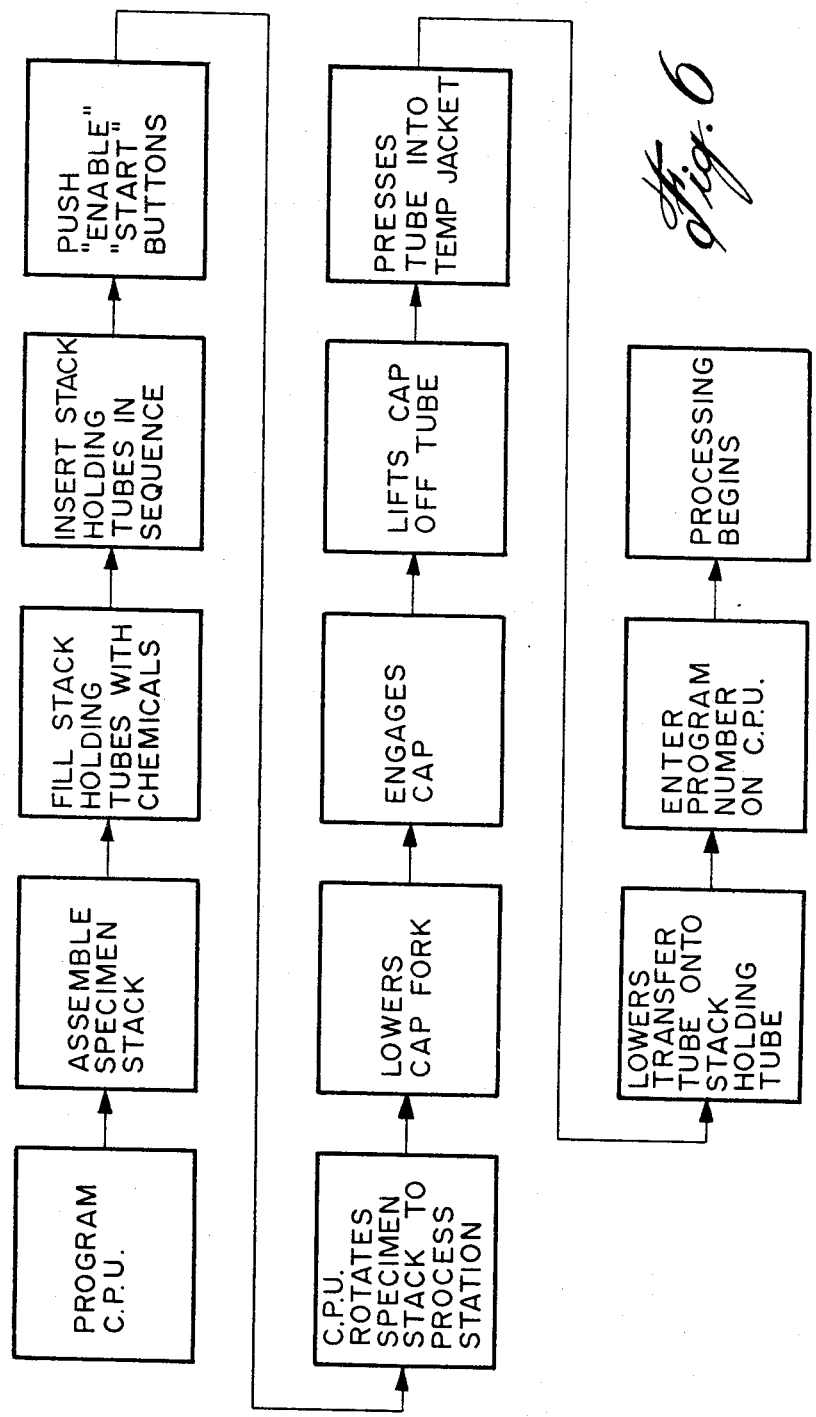
FIG. 6 is a flow chart of the start sequence.

The flow sheet for the start sequence from the central processing unit (CPU) is shown in FIG. 6.

The sequence of steps is as follows:

Program central processing unit (CPU).

Assemble specimen stack with tissues to be processed.

Top off stack with magnetic stainless steel actuator.

Insert stack assembly into stack holding tube and place into first of twenty two tube holes in carousel opposite start switch.

Fill required number of tubes with appropriate chemicals.

Insert capped tubes containing chemicals in sequence to be used in carousel.

Push "enable" switch.

Push "start" switch.

CPU recognizes a valid start sequence.

A. CPU rotates carousel to move the specimen stack holding tube opposite the processing station.

B. CPU lowers transfer coil assembly and attached cap removal fork.

C. CPU moves carousel inwards to engage tube cap and cap removal fork.

D. CPU raises the transfer coil assembly with the cap removal fork retaining the cap and thereby opens the specimen stack holding tube.

E. CPU moves carousel into the process station pressing the tube into the processing temperature control block.

F. CPU lowers the transfer coil assembly until the transfer tube and the open specimen stack holding tube are sealed together.

G. CPU blanks CPU display to prompt user to enter the two digit program number to be executed.

User enters two digit number program.

CPU turns on "start" switch lamp. Begins processing according to time, temperature and agitation parameters of the first step of the particular program.

Figure 7:
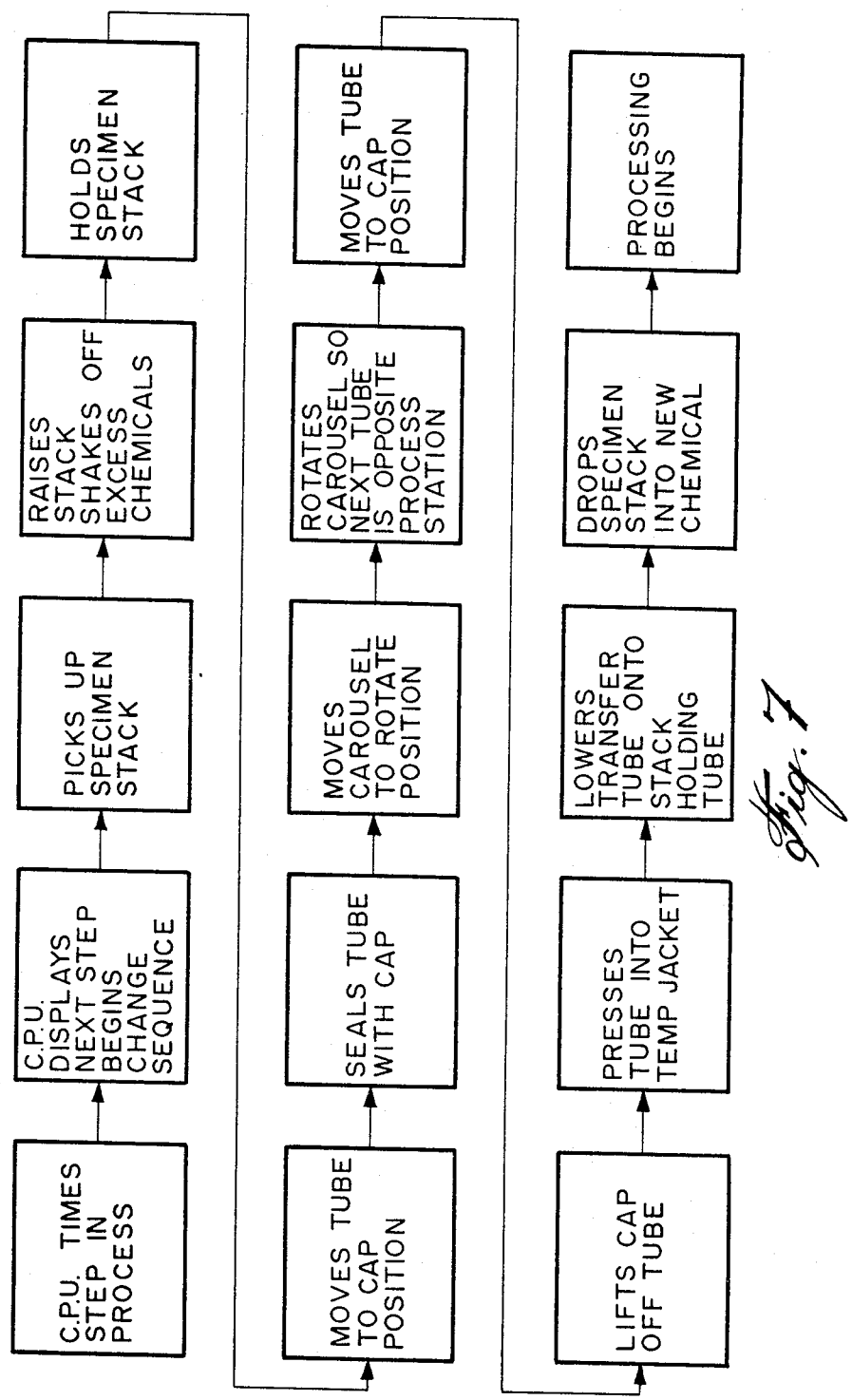
FIG. 7 is a flow chart of the chemical change sequence.

The flow sheet for the chemical change sequence is shown in FIG. 7. The sequence of steps is as follows:

CPU times out step in process.

CPU displays next step and begins change sequence.

A. CPU turns on the transfer electromagnetical coils top and bottom and picks up the specimen stack.

B. CPU raises the transfer coil assembly and the magnetically held specimen stack.

C. CPU shakes off excess chemicals in the specimen stack by turning the top magnetic transfer coil 40 on and off while keeping the bottom transfer coil 41 on continuously.

D. CPU turns on the hold electromagnetic coil when the stack and transfer assembly have cleared the tube and turns off the transfer coils top and bottom.

E. CPU moves the carousel out of the process station to the cap station.

F. CPU lowers the transfer coil assembly with the tube cap in the cap fork until the cap and the open tube are sealed together.

G. CPU moves the carousel back to the rotate position.

H. CPU rotates carousel so next tube with chemicals is opposite the processing station.

I. CPU moves the carousel inwards to engage the tube cap and cap removal fork.

J. CPU raises the transfer coil assembly with the cap removal fork retaining the cap, and thereby opens the tube.

K. CPU moves the carousel into the process station pressing the tube into the processing temperature control block.

L. CPU lowers the transfer coil assembly until the transfer tube and the open tube are sealed together.

M. CPU turns off the hold coil allowing the specimen stack to fall into the new chemical tube.

N. CPU begins processing according to time, temperature and agitation parameters of the new step of the particular program.

Various changes may be made to the different elements shown in the apparatus without departing from the scope of the present invention which is limited only by the following claims.

The embodiments of the invention in which an exclusive property or privilege is claimed, are defined as follows:

1. In an apparatus for treating samples of cellular materials wherein the samples are contained in a plurality of sample holders joined together to form a stack,
   the apparatus including at least one stack holding tube, open at the top, having a removable cap,
   positioning means to move the stack holding tube between a treatment position and a cap removal position,
   a transfer tube having a bottom opening positioned in the treatment position above the stack holding tube, and means to move the stack from the stack holding tube to the transfer tube,
   the improvement of a cap removable device comprising
   a fork means attached to the means to move the stack from the stack holding tube to the transfer tube,
   fork mating means on the removable cap, the fork means engaging the fork mating means when the means to move the stack is at a predetermined position, and the stack holding tube is moved to the cap removal position, and the cap is lifted when the means to move the stack is raised.

2. The apparatus according to claim 1 wherein a plurality of stack holding tubes are positioned in a circle about a vertical axis of a rotatable carousel, and including drive means for rotating the carousel, lateral movement means for moving the carousel into at least three positions representing rotating position, the cap removal position and the treatment position, and wherein the fork means engages with the cap when the stack holding tube on the carousel is moved from the rotating position to the cap removal position.

3. The apparatus according to claim 2 wherein the means to move the stack from the stack holding tube to the transfer tube comprises a moveable magnetic coil about the transfer tube which magnetizes a magnetizable member at the top of the stack, and the fork means for lifting the cap is connected to the moveable magnetic coil.

* * * * *